United States Patent
Oku et al.

(10) Patent No.: US 6,736,941 B2
(45) Date of Patent: May 18, 2004

(54) PROCESS FOR PURIFYING PROPYLENE OXIDE

(75) Inventors: Noriaki Oku, Ichihara (JP); Masaru Ishino, Sodegaura (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/258,411

(22) PCT Filed: Apr. 20, 2001

(86) PCT No.: PCT/JP01/03444

§ 371 (c)(1),
(2), (4) Date: Oct. 24, 2002

(87) PCT Pub. No.: WO01/83468

PCT Pub. Date: Nov. 8, 2001

(65) Prior Publication Data

US 2003/0102206 A1 Jun. 5, 2003

(30) Foreign Application Priority Data

Apr. 28, 2000 (JP) ............................ 2000-130342

(51) Int. Cl.[7] .................. B01D 3/34; C07D 301/32; C07D 303/04
(52) U.S. Cl. ................. 203/68; 203/70; 549/541
(58) Field of Search ................ 203/68, 69, 70, 203/100; 549/541

(56) References Cited

U.S. PATENT DOCUMENTS

| 3,338,800 A | | 8/1967 | Binning et al. |
|---|---|---|---|
| 3,350,418 A | | 10/1967 | Bowe et al. |
| 3,449,219 A | | 6/1969 | Schmidt |
| 3,909,366 A | * | 9/1975 | Schmidt et al. ............... 203/69 |
| 4,402,794 A | * | 9/1983 | Nemet-Mavrodin et al. .. 203/14 |
| 4,437,939 A | | 3/1984 | Bhise et al. |
| 5,262,017 A | | 11/1993 | Meyer et al. |
| 5,354,430 A | | 10/1994 | Culbreth, III et al. |
| 5,354,431 A | | 10/1994 | Taylor |
| 5,489,366 A | * | 2/1996 | Jongenburger ............... 203/14 |
| 6,500,311 B1 | * | 12/2002 | Sawyer ....................... 203/44 |

FOREIGN PATENT DOCUMENTS

| EP | 0 389 300 A1 | 9/1990 |
|---|---|---|
| EP | 0 673 935 A2 | 9/1995 |

OTHER PUBLICATIONS

Coulson et al, "Chemical Engineering" vol. Two Unit Operations 3rd Ed. 1977.*

* cited by examiner

*Primary Examiner*—Virginia Manoharan
(74) *Attorney, Agent, or Firm*—Sughrue Mion, PLLC

(57) ABSTRACT

A process is described for purifying propylene oxide, which includes the step of distilling propylene oxide containing impurities in the presence of a hydrocarbon having 5 carbon atoms or less. According to the present invention, a process is provided for purifying propylene oxide which has a feature that impurities contained in a solution containing propylene oxide to be purified can be efficiently removed. Oxygen-containing impurities, in particular, can be very efficiently removed.

3 Claims, 1 Drawing Sheet

PROCESS FOR PURIFYING PROPYLENE OXIDE

TECHNICAL FIELD

The present invention relates to a process for purifying propylene oxide. More particularly, the present invention relates to a process for removing efficiently impurities which exist in propylene oxide to be purified, especially, a process for purifying propylene oxide, which has a feature that impurities which contain an oxygen atom (hereinafter, may be referred to as "oxygen-containing impurities") can be removed very efficiently.

BACKGROUND ART

As a purification process of propylene oxide, a process in which water and a hydrocarbon having 8–10 carbon atoms are used as an extractant, an impurity of a hydrocarbon having 6 carbon atoms contained in propylene oxide is transferred to an oil layer, and a propylene oxide aqueous solution of a water layer is distilled, is known (JP05-170755A). Moreover, a process of distilling an alkylene glycol having 2 to 6 carbon atoms as an extractant is also known (U.S. Pat. No. 5,354,431). However, these processes were insufficient from a viewpoint of removing oxygen-containing impurities efficiently and economically.

DISCLOSURE OF THE INVENTION

Under the present situation, an object of the present invention is to provide a process for purifying propylene oxide, which has a feature that impurities exist in propylene oxide to be purified can be efficiently removed, especially oxygen-containing impurities can be very efficiently removed.

That is, the present invention relates to a process for purifying propylene oxide, which comprises distilling propylene oxide containing impurities in the presence of a hydrocarbon having 5 carbon atoms or less.

BRIEF EXPLANATION OF THE DRAWINGS

In FIG. 1, 1 shows a distillation column, 2 shows a feed line of low purity propylene oxide, 3 shows a feed line of a hydrocarbon, 4 shows a pipeline of impurities and 5 shows a pipeline of purified propylene oxide.

BEST MODE FOR CARRYING OUT THE INVENTION

Figure 1:
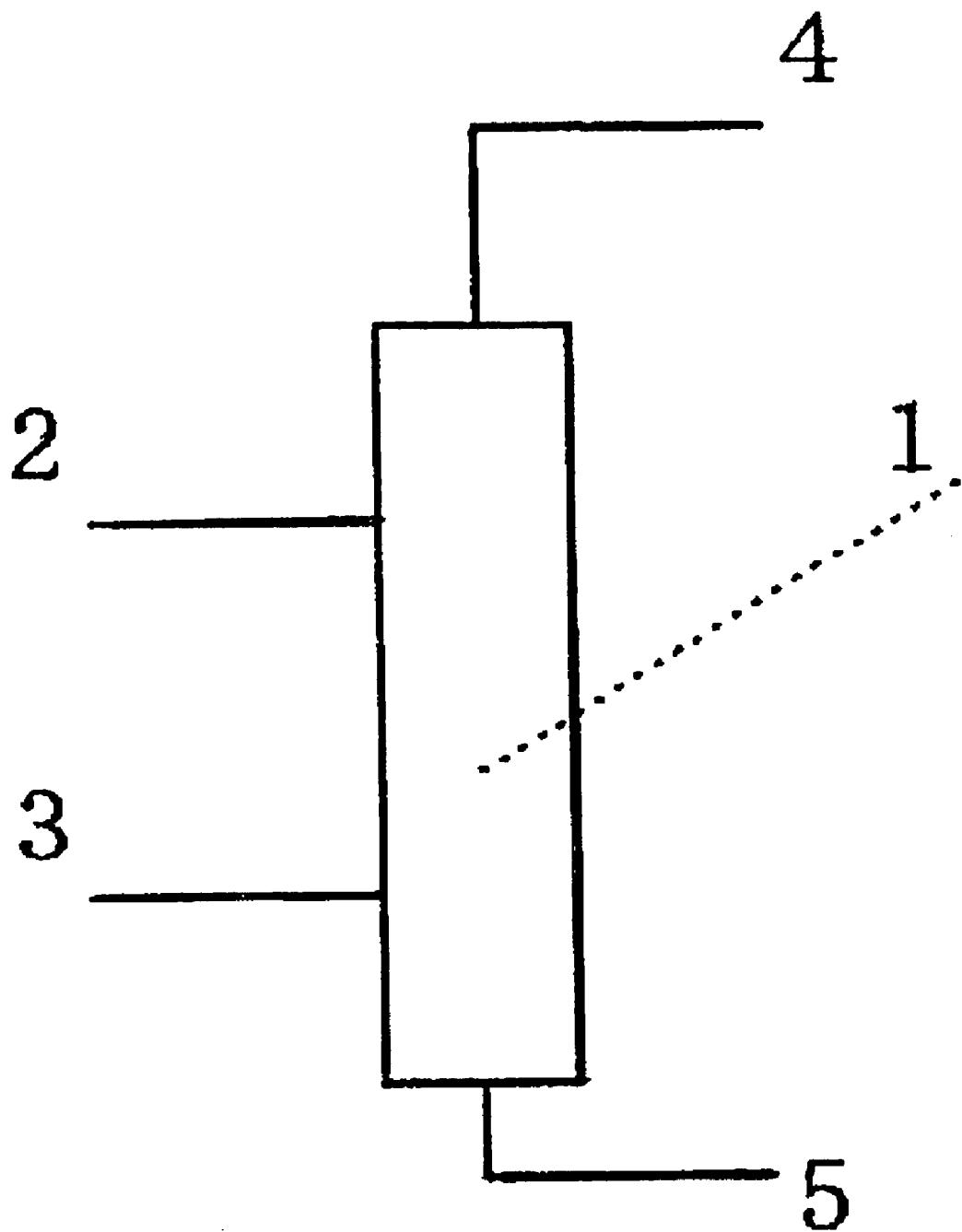
FIG. 1 is a figure showing an example of a desirable embodiment of the present invention.

Propylene oxide containing impurities to be subjected to purification of the present invention is not particularly restricted, and for example, crude propylene oxide which has been obtained by epoxidation or direct oxidation of propylene, can be applied.

Various impurities are usually contained in propylene oxide to be subjected to purification, and impurities containing oxygen atoms (oxygen-containing impurities) such as methanol, water, acetaldehyde and propionaldehyde are included therein.

The process of the present invention is effective in propylene oxide containing these oxygen-containing impurities, particularly, propylene oxide containing methanol and water of which separation is very difficult.

The concentration of oxygen-containing impurities in propylene oxide which is subjected to the process for purification of the present invention is usually 50 ppm by weight to 5% by weight in total.

As the hydrocarbon having 5 carbon atoms or less used in the present invention, there can be listed methane, ethane, ethylene, propane, propylene, n-butane, iosobutylene, n-pentane, 1-butene, 2-butene, isobutane, cyclopentadiene, cyclopentene, isoprene, cyclopentane, 1-pentene, 2-pentene, butadiene, etc., a hydrocarbon having 3–5 carbon-atoms is preferable, and a hydrocarbon having 4 or 5 carbon atoms is more preferable.

These hydrocarbons may be used alone or together with two or more kinds. The existing amount of the hydrocarbon is preferably 20 to 99.99% by weight at a upper part of a column where it is fed in the column, and more preferably 30–99.9% by weight. When the amount is to small, sufficient separation of the oxygen-containing impurities may become impossible because the impurities does not contact with the hydrocarbon sufficiently, and, on the other hand, when the existing amount is too large, it may distill from the bottom of the column, therefore may become a impurity of a propylene oxide.

In addition, the hydrocarbon flowed out from the column can be economically used by recovering and recycling to the column. When 2 or more kinds of hydrocarbons are used together, the existing amount is based on the total amounts of the hydrocarbons.

The hydrocarbon of the amount equal to the amount purged from the column may be fed to the column to allow to exist the hydrocarbon. The overhead gas of the column is condensed, then the condensate is contacted with water and settled, and the resulting water phase only is purged together with the oxygen-containing impurities to the outside of the system and the whole amount of the resulting oil phase is returned to the column as a reflux thereby to accumulate the hydrocarbon in the column and to reduce the makeup amount from the out of the system, and an efficient and economical operation becomes possible because the makeup amount of the hydrocarbon can be equal to only an amount of a part dissolved in the water phase by these operations.

A preferable embodiment of distillation in the present invention is explained with reference to FIG. 1. According to this embodiment, a low purity propylene oxide containing oxygen-containing impurities such as methanol, water and acetaldehyde of more than about 50 ppm by weight as a feeding material, is continuously fed in a distillation column 1 through a feeding line 2. At the same time, a hydrocarbon having 4 carbon atoms such as isobutylene is also continuously fed through feeding line 3, and contacted with it inside of the column, and the oxygen-containing impurities such as methanol and water are discharged together with the hydrocarbon from the top of the column through a feeding line 4, and propylene oxide in which the impurities have been removed is recovered from the bottom part of the column through a feeding line 5.

EXAMPLE

Example 1

Propylene oxide containing 0.2% by weight of water, 0.02% by weight of acetaldehyde, and 0.02% by weight of methanol is fed into a distillation column with 60 plate numbers. At the same time, butane is also fed at a lower part than the plate number into which propylene oxide is fed. Acetaldehyde, methanol, water and butane are discharged from the top part of the distillation column, and according to the simulation, the impurities in propylene oxide distilled from the bottom of the column are fully reduced to 10 ppm by weight of acetaldehyde, 5 ppm by weight of methanol, 10 ppm by weight of water and 10 ppm by weight of butane. In addition, the pressure of the top of the distillation column is 0.73 MPa, and the temperature is 63° C. As a refluxed amount in the operation, the flow rate ratio of a refluxed amount to a fed amount of propylene oxide is 3.

INDUSTRIAL APPLICABILITY

As described above, according to the present invention, a process for purifying propylene oxide which has a feature that impurities contained in propylene oxide to be purified can be efficiently removed, especially, oxygen-containing impurities can be very efficiently removed, can be provided.

What is claimed is:

1. A process for purifying propylene oxide, which consists essentially of distilling propylene oxide containing 50 ppm by weight to 5% by weight of oxygen-containing impurities in total in the presence of a hydrocarbon having 5 carbon atoms or less using a distillation column, discharging the oxygen-containing impurities together with the hydrocarbon from the top of the column, and recovering purified propylene oxide from the bottom of the column.

2. The process according to claim 1, wherein the hydrocarbon is a member selected from the group consisting of hydrocarbons having 3, 4, and 5 carbon atoms.

3. The process according to claim 2, wherein the hydrocarbon is a member selected from the group consisting of hydrocarbons having 4 and 5 carbon atoms.

* * * * *